US00PP15344P2

(12) United States Plant Patent
McNaughton

(10) Patent No.: US PP15,344 P2
(45) Date of Patent: Nov. 23, 2004

(54) ***LAVANDULA* PLANT NAMED 'LAVANG 21'**

(50) Latin Name: *Lavandula angustifolia*
Varietal Denomination: Lavang 21

(76) Inventor: Virginia McNaughton, Lavender Downs, Lawford Road, West Melton, RD6 Christchurch (NZ)

( * ) Notice: Subject to any disclaimer, the term of this patent is extended or adjusted under 35 U.S.C. 154(b) by 21 days.

(21) Appl. No.: 10/663,849

(22) Filed: Sep. 15, 2003

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—S B McCormick-Ewoldt

(57) ABSTRACT

A new cultivar of *Lavandula* plant named 'Lavang 21' that is characterized by vibrant violet corollas and rich violet-blue calyces, large bushy habit and very long, straight peduncles. These traits set it apart from all other existing varieties of *Lavandula* known to the inventor.

2 Drawing Sheets

Genus: *Lavandula.*
Species: *angustifolia.*
Denomination: Lavang 21.

BACKGROUND OF THE INVENTION

The present invention relates to a new and distinct cultivar of lavender known botanically as *Lavandula angustifolia* and hereinafter referred to by the cultivar name 'Lavang 21'. The new invention 'Lavang 21' is a hybrid resulting from the pollination between *Lavandula angustifolia* 'Twickel Purple' (unpatented) and an unidentified *Lavandula angustifolia* cultivar (unpatented). 'Lavang 21' was selected in a cultivated area of Christchurch, New Zealand by the inventor in 1995. The female parent plant is *Lavandula angustifolia* 'Twickel Purple' and the male parent plant is an unidentified *Lavandula angustifolia* cultivar.

The new lavender 'Lavang 21' is distinct and unique due to a bold upright habit, spike colour and striking presence. 'Lavang 21' is distinguishable from the parent plants by color of foliage and flower spike, shape and habit. There are no existing close comparison plants known to the inventor. 'Lavang 21' is distinguishable from all other lavenders known to the inventor by colour and size of spike, positioning of peduncles, foliage colour, shape of bush and upright habit.

The new invention 'Lavang 21' was asexually propagated by the inventor in Christchurch, New Zealand in 1997 using soft to semi-hardwood cuttings. Since that time subsequent generations have been determined fixed, stable and true to type.

SUMMARY OF THE INVENTION

The following traits have been repeatedly observed and represent the distinguishing characteristics of the new *Lavandula* cultivar 'Lavang 21'. These traits in combination distinguish 'Lavang 21' from all other existing varieties of *Lavandula* known to the inventor. 'Lavang 21' has not been tested under all possible conditions and phenotypic differences may be observed with variations in environmental, climatic, and cultural conditions, however, without any variance in genotype.

1. *Lavandula* 'Lavang 21' exhibits an upright, bushy habit.

2. *Lavandula* 'Lavang 21' exhibits the color combination of vibrant violet corollas and rich violet-blue calyces on each individual flower spike.
3. *Lavandula* 'Lavang 21' exhibits particularly long and upright peduncles for a *Lavandula angustifolia* cultivar.
4. *Lavandula* 'Lavang 21' exhibits a striking overall height for a *Lavandula angustifolia* cultivar.

BRIEF DESCRIPTION OF THE DRAWINGS

The accompanying color drawings illustrate the overall appearance of the new cultivar 'Lavang 21' showing colors as true as it is reasonably possible to obtain in colored reproductions of this type. Colors in the drawings may differ from the color values cited in the detailed botanical description, which accurately describe the actual colors of the new variety 'Lavang 21'. The illustrated plants have been grown in open ground out-of-doors in Christchurch, New Zealand. No chemicals were used to treat the plants, which are 4-years-old.

The drawing labeled as FIG. 1 shows the entire plant from a side view perspective, illustrating the upright habit and the long peduncles.

Figure 1:
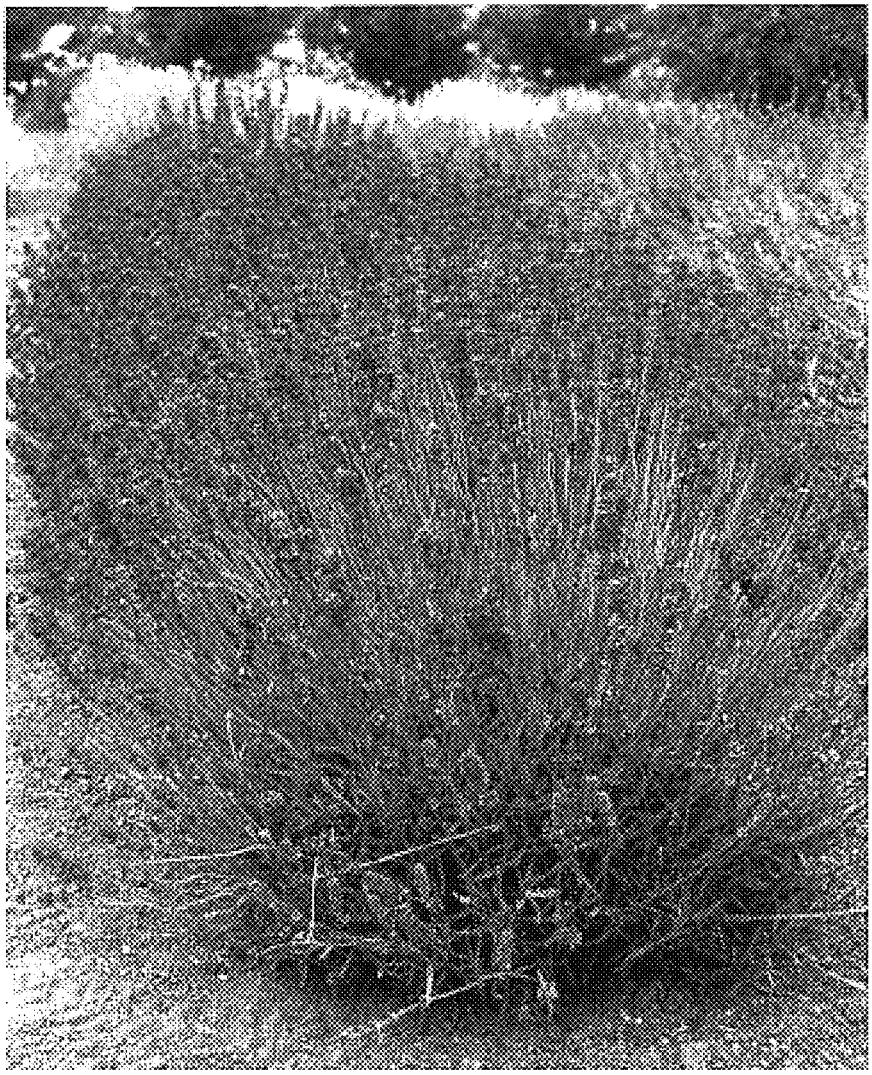
Figure 2:
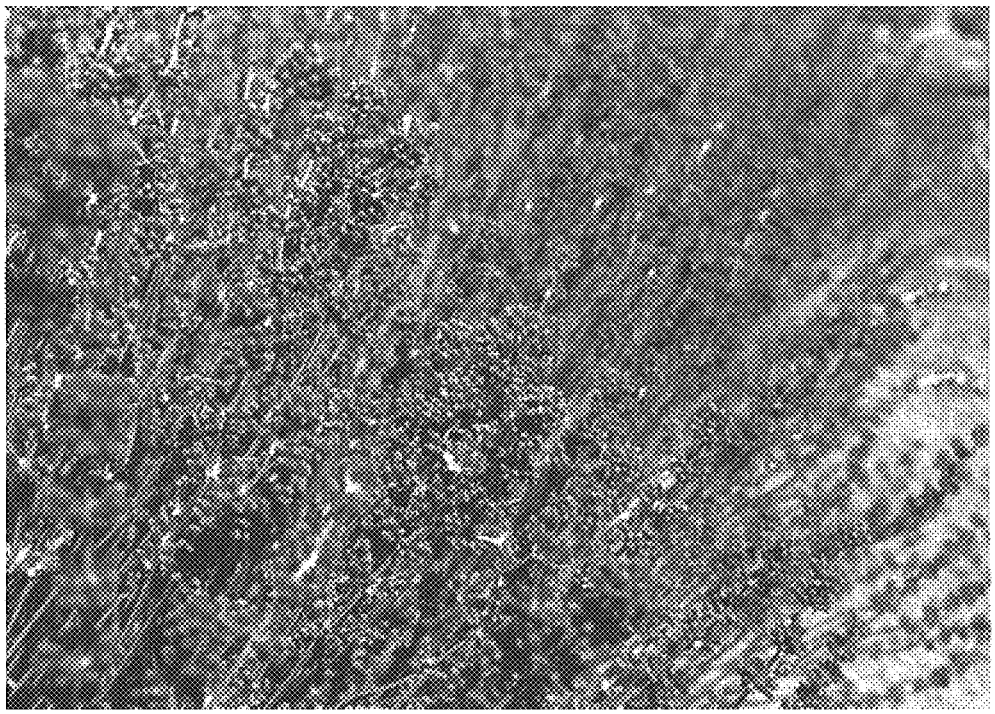

The drawing labeled as FIG. 2 shows a close-up of the flower spikes.

Both drawings are made using conventional photographic techniques and although foliage colors may appear different from actual colors due to light reflectance, they are as accurate as possible by conventional photography.

BOTANICAL DESCRIPTION OF THE PLANT

The following is a detailed description of the *Lavandula angustifolia* cultivar named 'Lavang 21'. Data was collected in West Melton, Canterbury, New Zealand from plants grown in the open ground and in dry conditions. The plants are 4-years-old and no chemicals were used to treat them. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. Color determination using The Royal Horticultural Society Colour Chart was conducted using the light box at The New Zealand Plant Variety Rights Office at Lincoln, Canterbury, New Zealand. Please note that the brown, green and violet ranges in these charts do not have an adequate color range to match that seen in lavender. The growing requirements are typical of the species and no disease problems have been observed.

Botanical classification: *Lavandula* 'Lavang 21'.
Species: *angustifolia.*
Common name: Lavender.
Parentage: 'Lavang 21' is a hybrid plant that resulted from the pollination of the following parent plants:
*Female parent plant.*—*Lavandula angustifolia* 'Twickel Purple'.
*Male parent plant.*—Unidentified *Lavandula angustifolia* cultivar.
Type: Aromatic perennial.
Commercial category: Ornamental shrub.
Use: Landscape plant for hedge, en masse, back of border, potted or feature plant.
Growth rate: Excellent for a *Lavandula angustifolia* cultivar.
Habit: Upright and bushy with ascending flower spikes.
Height: 70–80 cm in height.
Width: Approximately 70 cm in width.
Hardiness: Hardy to USDA Zone 5.
Disease susceptibility: In common with the species *Lavandula angustifolia*, Lavang 21 may be susceptible to Lavender leaf spot (*Septoria lavandulae*) or to bacterial blast (*Pseudomonas syringae*) or to Phoma if conditions are very wet or if plants are overwatered. Lavang 21 is not considered unusually or, in comparison with other known cultivars of the species, differently susceptible to any of these pathogens whose occurrence is more associated with adverse growing conditions.
Propagation method: Cuttings and tissue culture.
Root system: Fibrous.
Soil: Plant in well-drained soil.
Light levels: Plant in full sun.
Special needs: Prune after flowering to initiate second flowering period — will continue to flower if left but will need pruning prior to winter.
Time to initiate roots: 21 to 36 days are needed to develop roots on an unrooted cutting.
Time to develop to a one-gallon: 6 months are needed to produce a 1-liter container from a rooted cutting.
Branching habit: Foliage branched, erect, upright.
Seasonal interest: Vibrant violet flower spikes in June and July.
Stem:
*Stem shape.*—Square.
*Stem surface.*—Puberulent.
*Stem color.*—199B (grey-brown).
*Stem size.*—2–5 mm in diameter.
Foliage:
*Arrangement.*—Upright stems with whorls of leaves, arranged opposite along stem. A basal pair of leaves subtend each whorl of leaves. Regular arrangement of leaves along stems.
*Leaf division.*—Simple.
*Apices.*—More obtuse than acute.
*Base.*—Truncate to attenuate.
*Margins.*—Entire and revolute.
*Leaf shape.*—Linear.
*Color of mature leaves* (*upper surfaces*).—147A (dark olive-green).
*Color of mature leaves* (*lower surfaces*).—147B (olive-green).
*Color of young leaves* (*upper surfaces*).—189B (grey-green).
*Color of young leaves* (*lower surfaces*).—Too revolute to view.
*Upper and lower surfaces.*—Puberulent, older leaves more sparse covering.
*Venation.*—Mid vein depressed on upper surface and protruding beneath, side veins noticeable on lower surface with magnification.
*Internodes.*—2–2.5 cm in length.
*Foliar fragrance.*—Pleasantly sweet.
*Petiole.*—Sessile.
*Length of mature leaves.*—Approximately 0.8–3 cm in length.
*Width of mature leaves.*—1–2 mm in width.
Flower:
*Type of inflorescence.*—Terminal spike.
*Size of inflorescence.*—9–12 cm in length and 1.2–2 cm in width.
*Shape of inflorescence.*—Cylindrical with whorls of flowers arranged evenly along stem. Base whorl: 1–4 cm below main spike.
*Peduncles.*—30–35 cm in height and 1–2 mm in width.
*Peduncle position.*—Straight and very upright.
*Peduncle color.*—144A (yellow-green).
*Lateral branches on peduncle.*—Frequent, semi-stalked laterals with 1–5 flowers.
*Flower shape.*—Tubular.
*Corolla.*—Two-lipped with upper lip 2-lobed and lower lip 3-lobed.
*Corolla color.*—88A (vibrant violet).
*Bud color.*—89A (rich violet-blue).
*Calyx color.*—89A (rich violet-blue).
*Calyx surface.*—Densely pubescent.
*Bracteoles.*—Present but insignificant.
*Bracteole length.*—0.5 mm.
*Fertile bract size.*—Broad, approximately 4–5 mm×3.7 mm or smaller.
*Sterile bracts.*—Absent.
*Fragrance.*—Sweet.
*Blooming period* (*New Zealand*).—December and January.
*Blooming period* (*U.S.A.*).—June and July.
Reproductive organs:
*Stamens.*—4.
*Stamen length* (*2 posterior*).—1 mm.
*Stamen length* (*2 anterior*).—0.5 mm.
*Pistil.*—1.
*Pistil length.*—7 mm.
*Pistil diameter.*—Less than 0.25 mm.
*Filament diameter.*—Less than 0.25 mm.
*Filament color.*—Grayish-white.
*Style length.*—6 mm.
*Style color.*—Grayish-white.
*Stigma shape.*—Oval.
*Stigma color.*—Pale gray.
*Ovary shape.*—Oblong, globose.
*Ovary position.*—Superior.
*Ovary color.*—Green.
*Anther shape.*—Reniform.
*Anther length.*—Less than 0.2 mm.
*Anther color.*—Pale brown.
*Pollen amount.*—Sparse.
*Pollen color.*—Yellow-orange.
Seed:
*Seeds.*—Mostly-2 per calyx.
*Colour of seeds.*—202A.
*Length of seeds.*—1–2.5 mm. in length.

I claim:

1. A new and distinct variety of *Lavandula* plant named 'Lavang 21' as described and illustrated.

* * * * *